US012326438B2

(12) United States Patent
Tsuji et al.

(10) Patent No.: US 12,326,438 B2
(45) Date of Patent: Jun. 10, 2025

(54) HEALTH-LEVEL MEASURING METHOD, HEALTH-LEVEL DETERMINING APPARATUS, AND HAIR-HEALTH EXAMINATION SYSTEM

(71) Applicants: ORGAN TECHNOLOGIES INC., Tokyo (JP); RIKEN, Wako (JP)

(72) Inventors: Takashi Tsuji, Wako (JP); Koh-ei Toyoshima, Tokyo (JP)

(73) Assignees: ORGANTECH, INC., Tokyo (JP); RIKEN, Saitama (JP)

( * ) Notice: Subject to any disclaimer, the term of this patent is extended or adjusted under 35 U.S.C. 154(b) by 758 days.

(21) Appl. No.: 16/324,670

(22) PCT Filed: Aug. 8, 2017

(86) PCT No.: PCT/JP2017/028781
§ 371 (c)(1),
(2) Date: Feb. 11, 2019

(87) PCT Pub. No.: WO2018/030409
PCT Pub. Date: Feb. 15, 2018

(65) Prior Publication Data
US 2019/0170726 A1 Jun. 6, 2019

(30) Foreign Application Priority Data
Aug. 12, 2016 (JP) .................... 2016-158794

(51) Int. Cl.
*G01N 33/483* (2006.01)
*G01N 23/223* (2006.01)
(Continued)

(52) U.S. Cl.
CPC ....... *G01N 33/4833* (2013.01); *G01N 23/223* (2013.01); *G01N 33/48* (2013.01);
(Continued)

(58) Field of Classification Search
CPC .. G01N 33/4833; G01N 23/223; G01N 33/48; G01N 33/50; G01N 33/5005; A41G 5/004; G16H 50/30
See application file for complete search history.

(56) References Cited

U.S. PATENT DOCUMENTS 5,610,071 A 3/1997 Sabal
2007/0258561 A1* 11/2007 Chikawa ............. G01N 23/223
378/45

(Continued)

FOREIGN PATENT DOCUMENTS

JP H09-106427 A 4/1997
JP 2000-352566 A 12/2000
(Continued)

OTHER PUBLICATIONS

Kuzuhara et al., "Analysis of Internal Structure Changes in Black Human Hair Keratin Fibers with Aging Using Raman Spectroscopy", Biopolymers, vol. 87, No. 2-3, pp. 134-140. (Year: 2007).*
(Continued)

*Primary Examiner* — Kiho Kim
(74) *Attorney, Agent, or Firm* — Birch, Stewart, Kolasch & Birch, LLP

(57) ABSTRACT

The purpose of the present invention is to propose a method for measuring the level of health of a subject, with which it is possible: to perform health examination that is non-invasive to the human body and that employs a simple method; to provide highly reliable analysis results having a scientific basis; and to, additionally, provide appropriate solutions to the subject. Another purpose of the present invention is to propose a health-level determining apparatus employing said method and a new business model employing said method. The present invention is a method for measuring the level of health of a subject, including a hair analyzing step (A) for analyzing hair of the subject. It is
(Continued)

DERIVED FROM NON-AGA MALE | DERIVED FROM AGA MALE PATIENT
---|---
HAIR OF PARIETAL REGION (WHITE TERMINAL HAIR) | HAIR OF OCCIPITAL REGION (TERMINAL HAIR) | HAIR OF PARIETAL REGION (VELLUS HAIR) | HAIR OF INSIDE OF FOREARM (VELLUS HAIR)

90 μm · 87 μm · 40 μm · 32 μm preferable that the aforementioned hair analyzing step (A) include a step (A-1) for analyzing hair in the occipital region. In addition, it is preferable that the aforementioned hair analyzing step (A) include a step (A-2) for analyzing hair in a site other than the occipital region.

12 Claims, 6 Drawing Sheets

(51) Int. Cl.
　　　*G01N 33/48*　　　(2006.01)
　　　*G01N 33/50*　　　(2006.01)
　　　*A41G 5/00*　　　(2006.01)

(52) U.S. Cl.
　　　CPC ............. *G01N 33/50* (2013.01); *A41G 5/004* (2013.01); *G01N 33/5005* (2013.01)

(56) References Cited

U.S. PATENT DOCUMENTS

| 2016/0007908 A1* | 1/2016 | Guo | G01J 3/46 |
| | | | 348/77 |
| 2017/0115240 A1 | 4/2017 | Herron et al. | |
| 2017/0119130 A1* | 5/2017 | Witchell | G01N 21/31 |

FOREIGN PATENT DOCUMENTS

| JP | 2002-007566 A | | 1/2002 |
|---|---|---|---|
| JP | 2002-136503 A | | 5/2002 |
| JP | 2004-045133 A | | 2/2004 |
| JP | 2006-053101 A | | 2/2006 |
| JP | 4071891 B2 | * | 4/2008 |
| JP | 2008-249700 A | | 10/2008 |
| JP | 2008232674 A | * | 10/2008 |
| JP | 2014-052322 A | | 3/2014 |
| KR | 10-2013-0059803 A | | 6/2013 |
| WO | WO 2015/187874 A1 | | 12/2015 |

OTHER PUBLICATIONS

Serita et al., "Evaluation of human hairs with terahertz wave", Optical Engineering, vol. 53, No. 3, pp. 031205-1 to 031205-6. (Year: 2014).*

Chikawa et al., "Screening of breast cancer by elemental concentrations in hair observed by fluorescent X-ray analysis", Journal of Japanese Society for Synchrotron Radiation Research, vol. 18, No. 2, Mar. 2005, pp. 84-92.

International Search Report for PCT/JP2017/028781 (PCT/ISA/210) mailed on Nov. 7, 2017.

Written Opinion of the International Searching Authority for PCT/JP2017/028781 (PCT/ISA/237) mailed on Nov. 7, 2017.

Extended European Search Report issued Mar. 19, 2020, in European Patent Application No. 17839479.7.

Goldberg, L. J. and Y. Lenzy, "Nutrition and hair," Clinics in Dermatology (2010), vol. 28, pp. 412-419.

* cited by examiner

● MEASUREMENT RANGE ● CHANGE OF DISTANCE BETWEEN INFLECTION POINTS CAUSED BY AGING

● MEASUREMENT POSITION ● CHANGE OF POSITION OF INFLECTION POINT IN ZIGZAG HAIR SHAFT CAUSED BY AGING

HEALTH-LEVEL MEASURING METHOD, HEALTH-LEVEL DETERMINING APPARATUS, AND HAIR-HEALTH EXAMINATION SYSTEM

TECHNICAL FIELD

The present invention relates to a health-level measurement method, a health-level determination apparatus and a hair health examination system.

BACKGROUND ART

In a conventional health examination, a large number of tests including tests using various medical equipment, a blood test, a urine analysis and the like are carried out in a medical institution or the like to obtain information directly relating to diseases, for example, to determine whether or not an examinee takes a specific disease, or whether or not he/she needs to see a doctor in a medical institution.

On the other hand, as for a hair analysis, a chemical substance incorporated into hair is conventionally analyzed for verifying use of legally prohibited drugs such as an awakening drug, drugs prohibited for use in view of sports doping, pharmaceuticals such as a hypnotic, alcohol or the like, and exposure to an agricultural chemical, a harmful metal, an environmental pollutant or the like (see Patent Document 1). Besides, a method for simply diagnosing an unusual physical condition by measuring an amount of Ca in hair (see Patent Document 2), and a method for early detecting breast cancer on the basis of change of an amount of Ca in hair (see Non Patent Document 1) have been developed. In addition, a method for monitoring a situation of a living body on the basis of results of analyses on the amino acid composition and mineral of hair has been proposed (see Patent Document 3). However, it cannot be said that accuracy of these methods is sufficiently high.

PRIOR ART DOCUMENTS

Patent Document

Patent Document 1: JP 2008-232674 A
Patent Document 2: JP 2004-045133 A
Patent Document 3: JP 2000-352566 A

Non Patent Document

Non Patent Document 1: Hoshako (Journal of Japanese Society for Synchrotron Radiation Research), 18(2), 84-92, 2005

SUMMARY OF INVENTION

Technical Problem

Under these circumstances, there are great needs for a health examination using a non-invasive and easier method capable of providing a highly reliable diagnostic result based on scientific ground. Besides, as for information obtained by the health examination, there are demands for, in addition to those directly relating to diseases, information more closely connected to everyday life such as a health condition of a subject in a broad sense, including a state of stress, a degree of aging, and a degree of fatigue. Therefore, an object of the present invention is to provide a method of a health examination using a non-invasive and easier method capable of providing a highly reliable diagnostic result based on scientific ground, and particularly, a method for measuring the health-level of a subject (including information directly relating to diseases and a health condition in a broad sense including a presymptomatic disease state).

Solution to Problem

The present inventors have made earnest studies for solving the above-described problem, resulting in finding that a health condition of a subject can be accurately determined by analyzing hair, and thus, the present invention has been accomplished.

Hair has structural regularities at various levels. For example, it is known that hair is produced in a constant rhythm in hair matrix, and that hence a structural regularity found in an internal structure of hair derives from the rhythm of the hair production. The present inventors have found that there is a structural regularity in a medulla of hair, and that the regularity is affected by aging, and progression of a symptom of androgenetic alopecia or the like to cause loss of a medulla itself, loss of the regularity (continuity) and the like, and have analyzed such a state of hair to develop a method for accurately determining a health condition of a subject. Besides, there is a regularity derived from a constant rhythm, such as hair shaft curvature or cyclic bending, in wavy hair or curly hair of human hair, though there is a large difference depending on the race, and the same also applies to zigzag hair occupying almost all the hair of a rodent. The internal structure of hair and bending of the hair shaft are both structural change occurring along the temporal axis, and a hair cycle similarly having a high temporal regularity defined by the hair type can be also apprehended as one aspect of the regularity derived from the rhythm. The structural regularity in hair can be quantitatively measured with accuracy and comparative ease through observation with an optical microscope or the like. Specifically, the present invention provides the following:

[1] A method for measuring the health-level of a subject, including a hair analysis step (A) of analyzing hair of the subject;

[2] The method according to [1], in which the hair analysis step (A) includes a substep (A-1) of analyzing hair of an occipital region;

[3] The method according to [2], in which the hair analysis step (A) further includes a substep (A-2) of analyzing hair of a region other than the occipital region;

[4] The method according to any one of [1] to [3], in which the hair to be used for the hair analysis has undergone a marking treatment for specifying a time period;

[5] The method according to any one of [1] to [4], further including a comparison step (B) of comparing analysis data obtained in the hair analysis step (A) with analysis data of a population;

[6] The method according to any one of [1] to [5], in which the hair analysis is at least one selected from the group consisting of external structure analysis, internal structure analysis, property analysis, genetic analysis and composition analysis of the hair;

[7] The method according to [6], in which the external structure analysis is analysis of at least one selected from the group consisting of a cuticle and an optical characteristic;

[8] The method according to [6] or [7], in which the internal structure analysis is analysis of at least one selected from the group consisting of a cortex of hair, a medulla of hair, a melanin granule and a regularity of a hair shaft structure;

[9] The method according to [8], in which the regularity of the hair shaft structure is a structural regularity having a hierarchy derived from a hair production rhythm;

[10] The method according to any one of [6] to [9], in which the property analysis is analysis of at least one selected from the group consisting of strength of the hair, suppleness of the hair, a diameter of a hair shaft, a cross-sectional shape of the hair and a wavy state of the hair;

[11] The method according to any one of [6] to [10], in which the composition analysis is analysis of at least one selected from the group consisting of minerals, proteins, lipids, pigments and metabolites;

[12] The method according to any one of [6] to [11], in which the hair analysis includes at least internal structure analysis;

[13] A health-level determination apparatus, including: input means to which analysis data of hair of a subject is input; comparison means for performing comparison of the analysis data of the subject input through the input means with a distribution of analysis data of a population; and determination means for determining the health-level of the subject on the basis of a result of the comparison; and

[14] A hair health examination system, including: input means to which analysis data of hair of a subject is input; comparison means for performing comparison of the analysis data of the subject input through the input means with a distribution of analysis data of a population; and determination means for determining health of the subject on the basis of a result of the comparison, in which the determination means determines deviation of a state or a constitution of the subject by using, as the distribution of the analysis data of the population, a distribution of analysis data of other persons generated by taking the other persons as subjects, and determines change of the state or the constitution of the subject by using, as the distribution of the analysis data of the population, a distribution of the analysis data of the subject himself/herself collected in an evaluation period during which the state or the constitution of the subject is evaluated.

Advantageous Effects of Invention

According to the method for measuring the health-level of the present invention, a highly reliable health examination result based on scientific ground can be provided by using a non-invasive and easier method, specifically, hair analysis. In particular, hair can be regarded as a storage medium in which all information ranging from the present to a given past time period is stored, and therefore, according to the present invention, information on change of the health condition of a subject can be provided. Besides, when information obtained from hair is linked to various big data, a solution suitable for each individual can be provided, and furthermore, a novel product based on scientific ground can be developed in the fields of health care, hair care and the like.

DESCRIPTION OF EMBODIMENT

<Health-Level Measurement Method>

Figure 1:
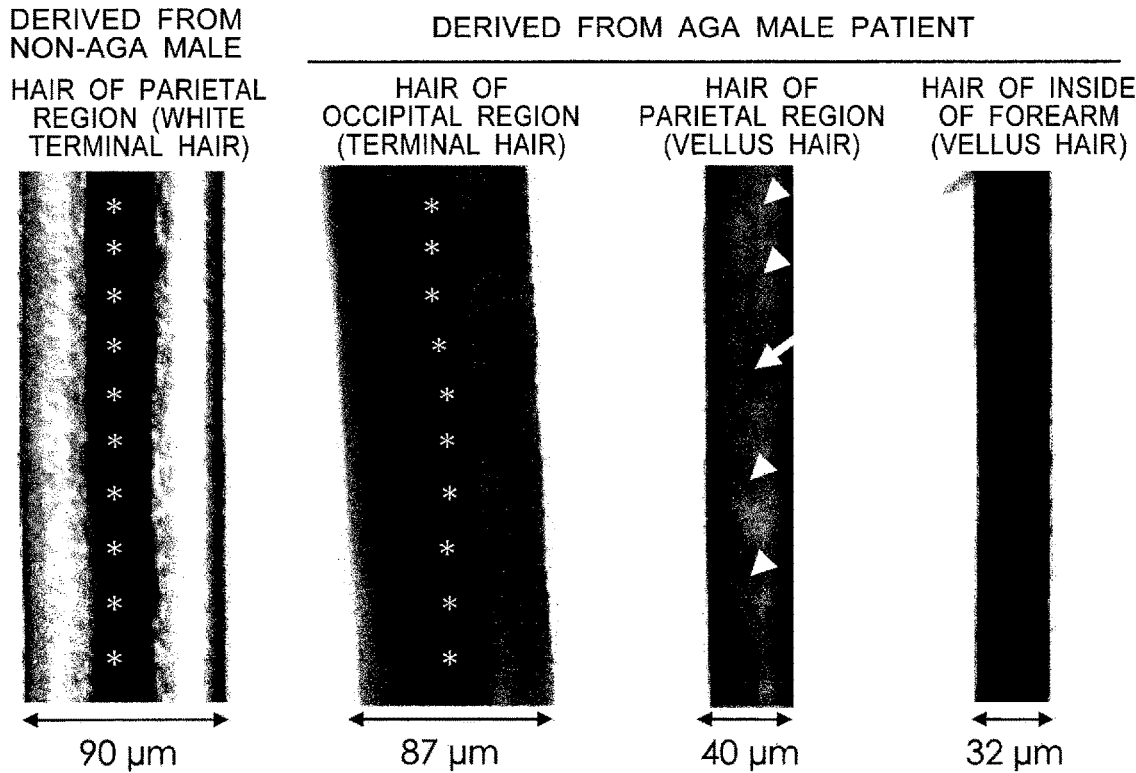
FIG. 1 is a diagram illustrating a diameter of a hair shaft and a form and morphology of a medulla of each hair type.

A health-level measurement method of the present invention is characterized by including a hair analysis step (A) of analyzing hair of a subject. Besides, the health-level measurement method of the present invention preferably includes a comparison step (B) of comparing analysis data obtained in the hair analysis step (A) with analysis data of a population. In this comparison step (B), the physical condition, a degree of fatigue, a degree of stress, a degree of aging, a state of exposure to or incorporation into the body of a specific element or chemical substance harmfully affecting health, a risk of a specific disease (including whether or not he/she is affected by the disease, and if affected, the extent of the disease, and the like), a risk of development of a specific disease (possibility of suffering from the disease in the future and the like) and the like of a subject can be quantitatively or qualitatively obtained by prescribed analysis/calculation processing.

The method of the present invention is non-invasive to the subject because hair is used as an analysis material, and is different from a conventional health examination, for example, in that an analysis sample can be easily collected painlessly, and that the analysis sample can be collected by the subject himself/herself without assistance from a medical professional if necessary. Besides, hair can be regarded as a storage medium in which all information ranging from the present to a given past time period is stored, and therefore, according to the present invention, information on change over time of the health condition of the subject can be known. In particular, according to the present invention, a novel parameter of a hair internal structure of a medulla or the like is used as an item of hair diagnosis in addition to conventionally known mineral analysis and external structure analysis, and therefore, a more accurate diagnostic result based on scientific ground can be provided. In addition, based on a result of the diagnosis, an appropriate solution can be provided to the subject if needed. Furthermore, a health-level determination apparatus and a novel business model for hair health examination utilizing the health-level measurement method of the present invention can be proposed. Now, the respective steps of the health-level measurement method of the present invention will be described in detail.

In the present invention, the term the health-level refers to an objective state of a health condition of a subject, and according to the present embodiment, it refers to a given reference value, or a relative health index to a given reference value and tendency of change thereof. Specifically, it refers to the health condition of the subject in a broad sense including a presymptomatic disease state, such as the physical condition, the degree of fatigue, the degree of stress, the degree of aging, a state of exposure to or incorporation into the body of a specific element or chemical substance harmfully affecting health, a risk of a specific disease (including whether or not he/she is affected by the disease, and if affected, the extent of the disease, and the like), and a risk of development of a specific disease (possibility of suffering from the disease in the future and the like). Besides, the physical condition, the degree of fatigue, the degree of stress and the degree of aging include not only these degrees in the whole body of the subject but also the degrees of the health-level of respective sites including hair, skin, nails, eyes, ears and the like. As the health-level of these, the physical condition, the degree of fatigue, the degree of stress, the degree of aging, a risk of a specific disease (including whether or not he/she is affected by the disease, and if affected, the extent of the disease, and the like), a risk of development of a specific disease (possibility of suffering from the disease in the future and the like) and the like are quantitatively or qualitatively obtained, based on data obtained in respective analysis items, by prescribed analysis/calculation processing.

The subject of the present invention may be a healthy person or a person affected by a disease, and is limited in none of the age, the race and the sex.

[Hair Analysis Step (A)]

The hair analysis step (A) of the present invention is a step of analyzing the hair of the subject by a specific analysis method.

The hair used in the analysis in the present invention may be collected in a test institution or the like by a person in charge of the test, or may be collected by the subject himself/herself. The collected hair may be sent to the test institution by mail. Since a hair sample is minute, the hair sample is assumed to be lost through influence of air flow, static electricity and the like, or there is a risk of inclusion of the hair of another person or another animal existing in the environment. Therefore, it is required to employ a method in which possible risks are minimized in handling the sample in each process of collection, transportation and analysis. For example, a collected hair shaft may be attached to an adhesive that does not affect the analysis process and can be easily removed by washing, or may be enclosed in an individually packable bag, and the resultant may be handled in a non-polar solution such as ethanol if necessary. Alternatively, for some analysis item, the subject can have his/her health-level measured merely by shooting a photograph of his/her hair by himself/herself and transferring data of the photograph to a test institution. For example, a simple method can be employed in which the subject transmits, by e-mail attachment, a photograph of his/her hair shot with a smartphone or the like by himself/herself to a test institution.

As the hair used for the analysis in the present invention, the collected hair may be directly used, or can be used after washing/pretreatment. Besides, a fallen hair sample including a hair root, or a cut hair sample not including a hair root can be used as the hair sample. Such a hair sample is cut in each position at a different distance from the hair root into a constant length to measure various components and the like therein, and a past history can be known based on change of the thus measured values. In other words, a hair growth rate is, although rather different among individuals, about 0.2 millimeters to 0.5 millimeters per day, and when this value is used, the state of the subject at an accurate time point in the past can be grasped. This is extremely suitable for grasping a cause of a living body situation influenced by a past history, such as a bad body condition derived from essential element deficiency or essential nutrient deficiency. Besides, not only the influence of such component deficiency but also the influence given to the subject during a given prescribed period, such as the degree of stress or damage caused by ultraviolet and the like, can be known.

Furthermore, in order to more accurately grasp the situation of the subject at an accurate time point in the past, the hair of the subject can be subjected to a marking treatment for specifying a time period. Examples of a method of the marking treatment include a method in which a hair shaft already grown on a body surface is subjected to a chemical treatment, and a method in which a marker substance is incorporated when hair is produced in a hair follicle. As the former method, a method in which a part of the hair shaft at a prescribed distance from the body surface is changed in color by using a hair dye or a hair bleach, and a marking method in which a growth rate is read by cutting a prescribed tip portion of the hair shaft are effective. As the latter method, a method in which, for the marking, a preparation containing an essential metal element, such as an iron, copper or zinc preparation, in an amount not affecting the health is orally administered for a short period of time is effective.

Hair includes a hair cuticle region, a cortex region and a medulla region. Cuticles are present in a surface portion of hair, and have a structure including a plurality of colorless transparent sheets stacked in a scaly form. A cell membrane complex (CMC) is present between the cuticles to adhere the cuticles to each other. Thus, hair is protected from an external stimulus, and hair components are prevented from flowing out to protect an internal portion of the hair. The cuticle region determines the shine and feel of the hair. Hair cortexes are in the shape of a cigar, and are vertically linked to one another to be arranged comparatively regularly. These hair cortexes adhere to one another in a lateral direction with a cell membrane complex (CMC) present in the cortex region, and have tensile strength in the lateral direction weaker than that in the vertical direction and hence are easily split in the form of split ends or the like. Besides, a melanin pigment is present in the cortex, and thus, the color of the hair is determined. The cortex region occupies 85 to 90% of the whole hair, and holds moisture therein to largely influence the strength of the hair. A medulla is basically present in a center portion of each hair, and many of its specific functions are not clarified yet. The present inventors have paid attention to the medulla, and have found that since a medulla structure is varied depending on the hair type, the age, the physical condition and the like, the health-level of the subject can be highly accurately measured by using, as one of indexes, a state of the hair internal structure of the medulla and the like.

(Analysis Items)

In a hair analysis method in the present invention, an appropriate analysis item can be selectively determined in accordance with information to be required. As the analysis item, the state of the internal structure of hair described above is preferably employed, and an additional analysis item as another health index is more preferably further employed in combination with the state of the internal structure of hair. Examples of the additional analysis item include external structure analysis, property analysis, genetic analysis, composition analysis and the like of hair.

An example of the internal structure analysis includes analysis of a regularity of the medulla of hair, the cortex of hair, the melanin granule, the hair shaft structure. For the analysis of these, discrimination and evaluation can be performed through observation with an optical microscope, an electron microscope or the like.

In human hair, the medulla is an internal structure found merely in terminal hair such as hair on the head, eyebrows, eyelashes, and a beard, sexual hair and the like growing after the development of secondary sexual characteristics, and is not found in downy hair or vellus hair. Therefore, the presence or the morphology of the medulla can be a significant index for discriminating terminal hair, vellus hair and an intermediate hair type from one another. The medulla may be, however, a structure not continuously present in the whole length of the hair shaft but is present discontinuously in some cases.

For the morphology of the medulla of hair, the continuity, the form, the thickness (diameter) or the like can be used as the analysis item. Besides, the medullas of human terminal hair are formed by a row of differentiated columnar epithelial cells stacked on one another, and are formed from fine fibers of a hair type characteristic hard keratins. The present inventors have found that the medulla structure has a constant rhythm in cooperation with the growth and differentiation of cells included in the medulla and the hair growth rate. The medulla includes, in a further inside portion, a colored granule or a vacuole and a fat-soluble component that are regarded to influence the optical characteristic and the mechanical characteristic of the hair shaft. Therefore, the morphology of the medulla is correlated with various characteristics peculiar to terminal hairs and the pathological condition of hair caused by alopecia or aging.

Specifically, in hair of the parietal region of a person presenting with juvenile or premature androgenetic alopecia at an early stage, the discontinuity of the medulla is remarkably found, and there is a tendency that the hair changes into nonmedullated hair with the medulla lost as the androgenetic alopecia progresses. In other words, when the presence, the thickness and the continuity of the medulla of hair are analyzed, the degree of progression and a risk of androgenetic alopecia can be determined, and the health-level of the hair of the subject can be thus measured. Also in a mature male not having a clear pathological condition of androgenetic alopecia, there similarly is a tendency that the medulla of hair of the frontal region or the parietal region becomes more discontinuous and deficient with the advance of age. In other words, when the change of the morphology of the medulla is quantitatively determined based on the discontinuity or a ratio of nonmedullated hair, quality change of the hair caused by aging can be measured.

The cortex is a main structure of hair, in which hard keratins form a fiber bundle parallel to the hair axis to generate high tensile strength peculiar to hair. Besides, melanin granules are dispersed in the cortex to generate a color tone as a colored hair. Hard keratin molecules contained in the cortex exist in a highly regular configuration, and are extremely stable owing to an SS bond between the hard keratin molecules and a rigid chemical cross-linkage through keratin-related molecular species. Since a heavy metal is incorporated into the hair shaft in such a cross-linking reaction, the hair shaft has a function as an excretory organ for the heavy metal. Therefore, the mechanical characteristic, the optical characteristic and the composition component are changed in accordance with the systemic health change or a nutritional factor and intake of essential metal elements and harmful heavy metal elements. Furthermore, it is also known that elution of components and denaturation are strongly caused through a chemical treatment such as daily hair washing and hair dyeing, and a heat treatment with a hair dryer.

A melanin granule is produced through production of a melanin pigment in the hair matrix by a melanocyte into which a daughter cell, which has been supplied from a pigment stem cell present in the hair follicle, changes through growth and differentiation. A melanocyte stem cell is reduced in number or exhausted owing to quality change of stem cell niche caused by aging, a chemical substance, exposure to radiation and the like. It is considered that as a result, hair turns gray due to aging and accumulation of an external factor over time in many cases. Besides, it is known that the growth and the differentiation of a pigment stem cell are in cooperation with a growth period of the hair follicle, and their influence on the quality change of the whole hair shaft is suggested.

As described above, the structure of the hair shaft has the structural regularity stacked so as to be perpendicular to the hair axis found in the medulla of hair and the structural regularity horizontal to the hair axis observed in the cortex and cuticle. These regularities can be regarded as a structural regularity having a hierarchy derived from the hair production rhythm. Since the hair is produced in a constant rhythm in the hair matrix, when the hair production rhythm is disturbed by any cause, the regularities of the hair shaft structure are affected. These regularities seem to be changed by change of cell kinetics in the hair follicle where the hair shaft is produced, or change of gene expression. Besides, there may be change caused by an external factor such as the environment and various treatments to which the hair is exposed. Accordingly, it is presumed that the various structural regularities found in the hair shaft and the disturbance of the regularities are in strong connection with the aging and the health condition at an individual level. The regularity of the hair shaft structure can be morphologically observed as an internal structure with an optical microscope, an electron microscope or the like. Besides, the regularity caused by the cross-sectional shape of the hair shaft and the morphology of the medulla can be also detected by using infrared tomography or a photoacoustic microscope. Furthermore, the regularity at a molecular level can be also detected by X-ray diffraction or mass analysis. When it is determined through the comparison step (B) described later that these hair shaft structures of the subject have no abnormality, the health-level can be determined to be high, and when it is determined that abnormality is detected in a part or the whole of the hair shaft structures, the health-level of the subject can be determined to be low. Besides, depending on the type of the hair shaft structure detected to have abnormality and the degree of the abnormality, a possibility of any of various diseases including hair-related diseases can be suggested.

An example of the external structure analysis includes analysis of the state of the cuticle structure or an optical characteristic.

The state of the cuticle structure can be observed with an optical microscope or the like. Since the cuticle structure is easily affected by stress, a psychological situation, a nutritional status, a living environment and the like, the health-level such as the degree of stress, the nutritional status, and the degree of aging of the subject can be measured by analyzing the cuticle structure of the subject. Besides, since the cuticle is a portion said to make the largest contribution to beauty in the property, the shine and the like of hair corresponding to the uppermost layer among the components of the hair, the health-level of the hair itself can be measured by analyzing the cuticle structure.

With respect to the optical characteristic, for example, when hair is irradiated with light to analyze the state of reflection/scattering, a light transmission amount and the like, inhomogeneity and the degree of luster of the hair can be known. Since the inhomogeneity and the luster of hair are varied depending on the age, the physical condition and the like of the subject, the health-level of the subject and the health-level of the hair itself can be measured by analyzing the optical characteristic of the hair.

An example of the property analysis includes analysis of the strength of the hair, suppleness of the hair, a hair shaft diameter, the cross-sectional shape of the hair, the wavy state of the hair or the like.

The genetic analysis can be performed by calculating an expression level of a specific gene by using a genomic DNA and a mitochondria DNA stably stored in a hair sample. Alternatively, the genetic analysis can be performed by calculating an expression level of a specific gene by using, as a sample, an mRNA contained in an epithelial cell (root sheath cell) adhering to the bottom of the hair shaft of the collected hair. In the genetic analysis of the present invention, an expression level of a gene is calculated as an absolute value or a relative value (such as a ratio to or a difference from that of a comparison object or a standard expression level). Besides, a DNA can be detected, as a characteristic in the sequence, in the form of change of SNPs or triplet repeat, or deletion or duplication of a part of or a genetic locus in a specific gene sequence.

The "specific gene" whose expression level is checked in the genetic analysis is not especially limited as long as it is a gene relating to the health-level of the subject or a gene corresponding to a race or a consanguineous group having a specific genetic characteristic. A gene relating to the health-level of the subject can be identified by an experiment using a microarray or the like. Examples of the specific gene include androgen receptor, a gene coding type II 5α reductase, and various nuclear transcription factors affecting traits of mitochondria DNA and the hair shaft.

An example of the composition analysis includes analysis of minerals (sodium, potassium, magnesium, calcium, chromium, molybdenum, manganese, iron, copper, zinc, phosphorus, selenium, iodine, lithium, vanadium, cobalt, nickel, boron, germanium, bromide beryllium, cadmium, mercury, aluminum, lead, arsenic), proteins, lipids, pigments, metabolites or the like. Examples of an analysis method for minerals include atomic absorption spectrometry and fluorescent X-ray spectroscopy using an electron microscope. A content or a distribution of a specific protein can be grasped based on a stained state depending on staining conditions, or can be quantitatively determined based on a transmission or total reflection infrared absorption spectrum.

It is known that minerals of hair are reduced in amount in modern society because of influences of lack of sleep, food contaminated with an additive, an agricultural chemical or environment, dietary habits, stress and the like. The health-level of the subject can be measured by measuring a content in hair of, for example, minerals essential for a human, such as sodium, potassium, magnesium, calcium, chromium, molybdenum, manganese, iron, copper, zinc, phosphorus, selenium and iodine. Specifically, when it is determined through the comparison step (B) described later that the content of these essential minerals in the hair of the subject falls in a normal range, the health-level of the subject can be determined to be high, and when it is detected that the content is out of the normal range but is at an abnormal level, the health-level of the subject can be determined to be low. Besides, depending on the type of mineral detected at an abnormal level, a possibility of any of various diseases can be suggested. Furthermore, when the content of these essential minerals is small, intake of a supplement or food capable of supplementing these can be appropriately proposed.

Harmful minerals such as mercury and cadmium are accumulated in hair in accordance with aging and the living environment, but the essential minerals such as potassium, magnesium and iron tend to be reduced in amount. Therefore, minerals particularly correlated with the age are picked up from hair measurement data, and the degree of aging of the subject can be determined in accordance with a prescribed calculation formula.

The hair analysis step (A) preferably includes a substep (A-1) of analyzing hair of the occipital region. Since the hair of the occipital region is stable in the structure as compared with hair of the other regions, a stable analysis result can be obtained. When the hair used as an analysis sample of the present invention is hair of the occipital region, a more stable and more reliable analysis result than in a conventional method can be obtained.

The hair analysis step (A) preferably further includes a substep (A-2) of analyzing hair of a region different from the occipital region. When an analysis result of the hair of the occipital region of the subject is compared with an analysis result of the hair of another region changing more sensitively to change of the environment, change of the physical condition, the aging and the like, the health-level of the subject can be more sensitively determined.

[Comparison Step (B)]

The health-level measurement method of the present invention includes the comparison step (B) of comparing the analysis data obtained in the hair analysis step (A) with a distribution of analysis data of a population. As the population, a distribution of analysis data of other persons generated by taking the other persons as subjects, that is, what is called big data, can be used. For comparing the analysis data of an individual obtained in the hair analysis step (A) with the distribution of the analysis data of the other persons, the analysis data may be compared with a population of the whole analysis data of the other persons, or may be compared with a specific population selected in accordance with the age, the sex, the residence area or the like.

A step of comparing data obtained in the substep (A-2) of analyzing the hair of a region different from the occipital region of the subject with data obtained in the substep (A-1) of analyzing the hair of the occipital region may be included in the comparison step (B). When the analysis result of the hair of the occipital region of the subject is compared with an analysis result of the hair of another region changing more sensitively to change of the environment, change of the physical condition, the aging and the like, the health-level of the subject can be more sensitively determined.

In the comparison step (B), the data of the hair of the individual obtained in the hair analysis step (A) can be analyzed to check change over time of the health-level of the subject. Specifically, since hair can be regarded as a kind of storage medium, the change over time of the health-level of the subject can be checked through comparison of data of respective portions at different distances from the hair root.

In this case, the hair of the subject has preferably undergone the marking treatment for specifying a time period.

The data obtained by the analysis of the hair analysis step (A) is compared with the distribution of the appropriate population in the comparison step (B), and thus, the healthy-level such as the physical condition, the degree of fatigue, the degree of stress, the degree of aging, a risk of a specific disease (including whether or not he/she is affected by the disease, and if affected, the extent of the disease, and the like), and a risk of development of a specific disease (possibility of suffering from the disease in the future and the like) of the subject can be quantitatively or qualitatively obtained by prescribed analysis/calculation processing.

<Health-Level Determination Apparatus>

[Health-Level Determination Apparatus for Individual User]

The present invention includes an invention of a health-level determination apparatus for determining the health-level of a subject on the basis of hair analysis data. The health-level determination apparatus of the present invention will be described with reference to FIG. 9. Specifically, the health-level determination apparatus 1 of the present invention includes input means 3 to which analysis data of hair of a subject is input, comparison means 4 for performing comparison of the analysis data of the subject input through the input means with a distribution (internal DB 5 and external DB 6) of analysis data of a population, determination means 7 for determining the health-level of the subject on the basis of a result of the comparison, and communication means 8 for informing the subject of a determination result. Information supplied from the communication means 8 is also accumulated in the internal DB 5. Besides, the health-level determination apparatus 1 of the present invention may include hair analysis means 2 for analyzing hair, or the hair analysis means may be provided in an apparatus different from the health-level determination apparatus 1.

(Hair Analysis Means)

An individual user (subject) provides his/her hair to the hair analysis means 2. A method for providing the hair is not especially limited, and the hair may be collected in an institution for performing the hair analysis, or may be collected by the subject himself/herself to be provided by means of mail or the like. For example, the hair sample is preferably attached to an adhesive sheet or enclosed in an individually packable bag so as not to be mixed with another sample. Besides, the hair sample may be transferred to a contact organization under normal temperature condition or may be transferred under low temperature condition of about 4° C. Various personal information accompanying the hair sample may be input to an internet site or the like provided with sufficient security. The hair sample and the related personal information can be collated with each other using an anonymization number or the like given to both of these. The provided hair is analyzed in the hair analysis means 2. In the hair analysis means 2, various analyses (analysis A, analysis B, analysis C, etc.) are carried out. As for specific analysis items and analysis methods, the description given with respect to the health-level measurement method of the present invention can be applied.

(Comparison Means)

Respective analysis data (A, B, C, etc.) obtained by the hair analysis means 2 and the personal information and the like of the subject are input by the input means 3, and compared with data of internal database (internal DB 5) and/or external database (external DB 6) in the comparison means 4. When past data of the subject is held in the internal DB 5, the comparison with this data can be carried out, and thus, change over time of the health-level of the subject can be checked. Besides, when the analysis data obtained by the hair analysis means 2 include data of the hair of the occipital region of the subject and data of the hair of a region other than the occipital region, these data can be compared with each other. Furthermore, when the analysis data obtained by the hair analysis means 2 is data of respective portions of the hair of the subject at different distances from the hair root, these data can be compared with one another.

(Determination Means)

The determination means 7 determines the health-level of the subject on the basis of a result of the comparison of the analysis data carried out in the comparison means 4 also in consideration of the personal information of the subject (the age, the sex, the residence area, the occupation, the height, the weight, the medical history, the state of stress, the daily habit information, the taste for food and drink and the like). Based on a result of the hair analysis, the physical condition, the degree of fatigue, the degree of stress, and the degree of aging of the subject can be determined. In addition, not only determination on each of these degrees in the whole body of the subject but also determination on the health-level of the hair itself can be made. The determination means 7 can not only determine the health-level of the subject but also present a solution if there is any problem in the health-level of the subject. Besides, a proposal for improving the health-level of the subject can be made.

(Communication Means)

The subject is notified of a result of the determination made by the determination means by the communication means 8. A notifying method is not especially limited, but is preferably notification by email, notification by mail or the like. Since the result of the determination can be also accumulated in the internal DB 5, the accuracy of the health-level determination apparatus of the present invention is improved as the number of determinations made by the apparatus increases.

The subject having received the result of the determination may practice, for a prescribed period of time, a solution for the health-level or a method for improving the health-level presented together with the result of the determination, and can have his/her health-level determination again by the health-level determination apparatus of the present invention to check the effect.

[Health-Level Determination Apparatus for Product Development Company]

The present invention also encompasses an invention of a health-level determination apparatus to be usefully used in product development in a product development company by determining the health-level of each panelist (subject) on the basis of hair analysis data. The health-level determination apparatus of the present invention will now be described with reference to FIG. 10. Specifically, the health-level determination apparatus 1 of the present invention includes input means 3 to which analysis data of hair of each panelist is input, comparison means 4 for performing comparison of the analysis data of each panelist input through the input means with a distribution (internal DB 5 and external DB 6) of analysis data of a population, determination means 7 for determining the health-level of each panelist on the basis of a result of the comparison, and communication means 8 for informing the product development company of a result of determination. Information supplied from the communication means 8 is also accumulated in the internal DB 5. Besides, the health-level determination apparatus 1 of the present invention may include hair analysis means 2 for analyzing hair, or the hair analysis means may be provided in an apparatus different from the health-level determination apparatus 1.

(Hair Analysis Means)

The product development company provides hair, which has been provided by a plurality of panelists, to the hair analysis means 2. A method for providing the hair is not especially limited, and the hair may be collected in an institution for performing the hair analysis, or may be collected by the panelist himself/herself to be provided by means of mail or the like. For example, the hair sample is preferably attached to an adhesive sheet or enclosed in an individually packable bag so as not to be mixed with another sample. Besides, the hair sample may be transferred to a contact organization under normal temperature condition or may be transferred under low temperature condition of about 4° C. Various personal information accompanying the hair sample may be input to an internet site or the like provided with sufficient security. The hair sample and the related personal information can be collated with each other using an anonymization number or the like given to both of these. The provided hair is analyzed in the hair analysis means 2. In the hair analysis means 2, various analyses (analysis A, analysis B, analysis C, etc.) are carried out. As for specific analysis items and analysis methods, the description given with respect to the health-level measurement method of the present invention can be applied.

(Comparison Means)

Respective analysis data (A, B, C, etc.) obtained by the hair analysis means 2 and the personal information and the like of each panelist are input by the input means 3, and compared with data of internal database (internal DB 5) and/or external database (external DB 6) in the comparison means 4. When past data of each panelist is held in the internal DB 5, the comparison with this data can be carried out, and thus, an effect of a product under development can be checked. Besides, when the analysis data obtained by the hair analysis means 2 includes data of the hair of the occipital region of the each panelist and data of the hair of a region other than the occipital region, these data can be compared with each other. Furthermore, when the analysis data obtained by the hair analysis means 2 is data of respective portions of the hair of each panelist at different distances from the hair root, these data can be compared with one another.

(Determination Means)

The determination means 7 determines the health-level of each panelist on the basis of on a result of the comparison of the analysis data carried out in the comparison means 4 also in consideration of the personal information of each panelist (the age, the sex, the residence area, the occupation, the height, the weight, the medical history, the state of stress, the daily habit information, the taste for food and drink and the like). Based on a result of the hair analysis, the physical condition, the degree of fatigue, the degree of stress, and the degree of aging of each panelist can be determined. In addition, not only determination on each of these degrees in the whole body of each panelist but also determination on the health-level of his/her hair itself can be made. A solution can be presented if there is any problem in the health-level of each panelist. Besides, a proposal for improving the health-level of each panelist can be made. In other words, the determination means 7 can not only determine the health-level of each panelist but also provide an analysis result of a tendency found in the whole panelists.

(Communication Means)

The product development company is notified of a result of the determination made by the determination means by the communication means 8. A notifying method is not especially limited, but is preferably notification by email, notification by mail or the like. Since the result of the determination can be also accumulated in the internal DB 5, the accuracy of the health-level determination apparatus of the present invention is improved as the number of determinations made by the apparatus increases.

The product development company having received the result of the determination can use the result of the determination for developing a product of its own. Besides, the product development company can ask for the determination by the health-level determination apparatus of the present invention again in order to check an effect of a product developed by itself <Hair Health Examination System>

The present invention also encompasses a hair health examination system that is a health examination system utilizing hair analysis. The hair health examination system of the present invention corresponds to various business models using the above-described health-level determination apparatus embodied by means of a system. Specifically, the hair health examination system includes the health-level determination apparatus of the present invention and a terminal that transmits/receives, through a communication network, hair analysis data/health examination results and the like to/from the health-level determination apparatus.

The present invention provides a hair health examination system including: input means to which analysis data of hair of a subject is input, comparison means for performing comparison of the analysis data with a distribution of analysis data of a population, and a determination means for determining the health-level of the subject on the basis of a result of the comparison, in which the determination means determines deviation of a state or a constitution of the subject by using, as the distribution of the analysis data of the population, a distribution of analysis data of other persons generated by taking the other persons as subjects, and determines change of the state or the constitution of the subject by using, as the distribution of the analysis data of the population, a distribution of the analysis data of the subject himself/herself collected in an evaluation period during which the state or the constitution of the subject is evaluated.

Figure 9:
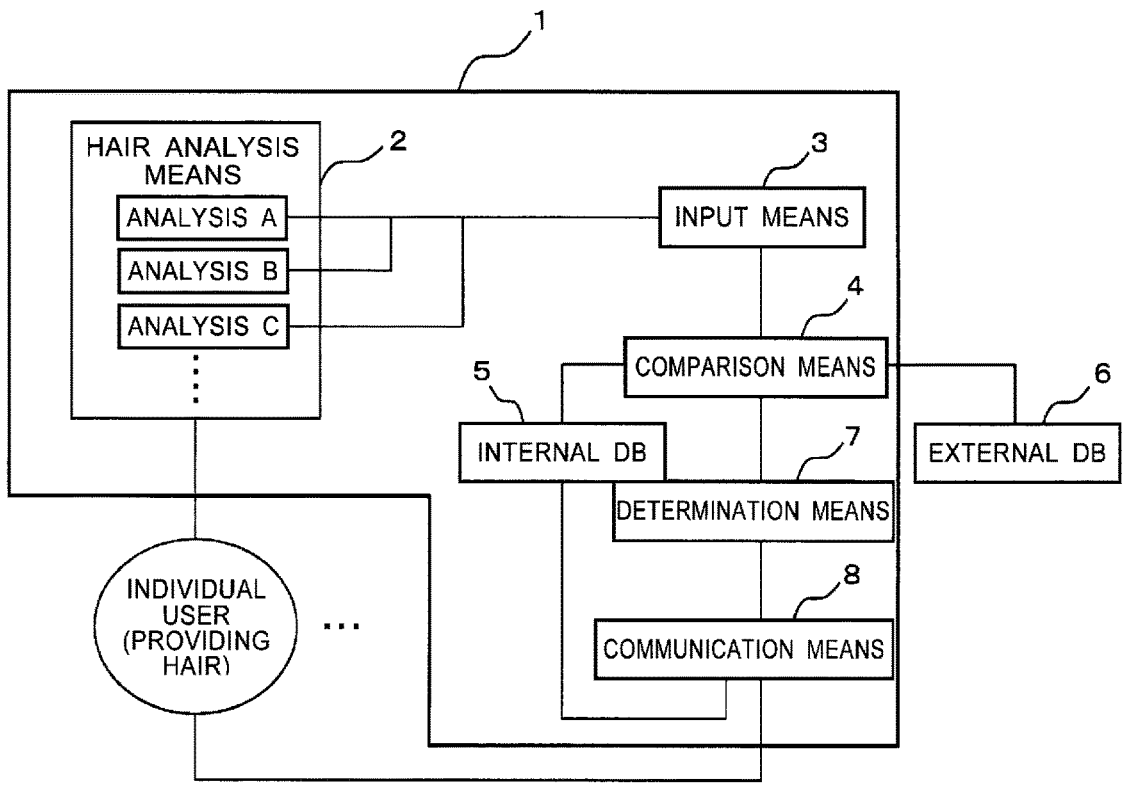
FIG. 9 is a conceptual diagram of a hair health examination system including a health-level determination apparatus of the present invention to be used for an individual user.
Figure 10:
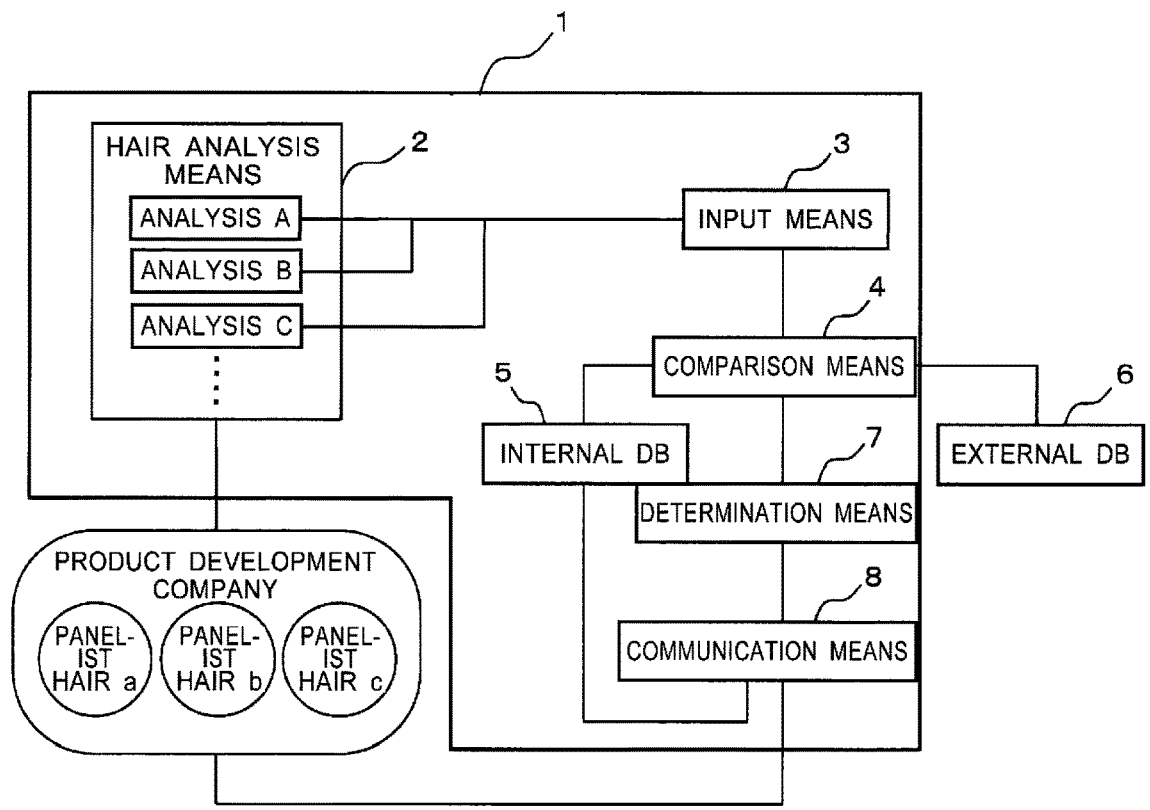
FIG. 10 is a conceptual diagram of a hair health examination system to be employed by a product development company.

Conceptual diagrams of the hair health examination system of the present invention are illustrated in FIG. 9 and FIG. 10. Specifically, the hair health examination system of the present invention is a hair health examination system including a health-level determination apparatus 1, and various terminals that transmit/receive, through a communication network, hair analysis data/health examination results and the like to/from the health-level determination apparatus 1. Specifically, the health-level determination apparatus 1 of the present invention includes input means 3 to which analysis data of hair of a subject is input, comparison means 4 for performing comparison of the analysis data of the subject input through the input means with a distribution (internal DB 5 and external DB 6) of analysis data of a population, determination means 7 for determining the health-level of the subject on the basis of a result of the comparison, and communication means 8 for informing the subject of a determination result. Information supplied from the communication means 8 is transmitted to a terminal (user terminal) of the subject and is also accumulated in the internal DB 5. The information supplied from the communication means 8 not only may be electronically transmitted to the subject but also may be provided in the form of a print from the terminal Besides, the health-level determination apparatus 1 of the present invention may include hair analysis means 2 for analyzing hair, or the hair analysis means may be provided in an apparatus different from the health-level determination apparatus 1.

One embodiment of the hair health examination system of the present invention will now be described (FIG. 9). A subject (user) transmits, from a user terminal to a communication terminal of the hair health examination system, his/her basic information and his/her answer to a specific questionnaire, and sends his/her hair to a designated analysis institution. The subject may go to the analysis institution to have his/her hair collected. For example, the hair sample is preferably attached to an adhesive sheet or enclosed in an individually packable bag so as not to be mixed with another sample. Besides, the hair sample may be transferred to a contact organization under normal temperature condition or may be transferred under low temperature condition of about 4° C. In the analysis institution (hair analysis means), analysis of an analysis item selected by the subject in the questionnaire is carried out. The basic information, the answer to the questionnaire and an analysis result of the hair of the subject are recorded in a personal (electronic) medical chart. Various personal information accompanying the hair sample is preferably input to an internet site or the like provided with sufficient security. The hair sample and the related personal information can be collated with each other using an anonymization number or the like given to both of these. In the analysis institution, analysis data is transmitted to a comparison terminal (comparison means 4), and is compared, in the comparison terminal, with data of a population or a part of the population stored in the internal DB 5 and/or the external DB 6, or a precedently set reference value, and thus, prescribed calculation processing is performed. A hair health examination result including information on the health-level calculated by the calculation processing, a proposal for improving the health-level, a proposal of a solution regarding an item having a problem in the health-level and the like is transmitted to the user terminal. The hair health examination result and the like are also recorded in the personal medical chart to be stored.

In addition to the embodiment in which each individual user uses the hair health examination system of the present invention, there can be an embodiment in which, for example, a beauty parlor (beauty salon) or a product development company uses the hair health examination system of the present invention. This embodiment will be described with reference to FIG. 10. From a terminal of the beauty parlor (beauty salon) or the product development company to a communication terminal of the hair health examination system, basic information of a customer and an answer of the customer to a specific questionnaire or the like are transmitted, and hair of the customer is sent to a designated analysis institution. For example, the hair sample is preferably attached to an adhesive sheet or enclosed in an individually packable bag so as not to be mixed with another sample. Besides, the hair sample may be transferred to a contact organization under normal temperature condition or may be transferred under low temperature condition of about 4° C. In the analysis institution (hair analysis means), analysis on an analysis item precedently selected is carried out. The basic information, the answer to the questionnaire and an analysis result of the hair of the subject are recorded in a personal (electronic) record. Various personal information accompanying the hair sample is preferably input to an internet site or the like provided with sufficient security. The hair sample and the related personal information can be collated with each other using an anonymization number or the like given to both of these. In the analysis institution, analysis data is transmitted to a comparison terminal (comparison means 4), and is compared, in the comparison terminal, with data of a population or a part of the population stored in the internal DB 5 and/or the external DB 6, or a precedently set reference value, and thus, prescribed calculation processing is performed. A hair health examination result including information on the health-level calculated by the calculation processing, a proposal for improving the beauty parlor or the product development company, a proposal of a solution regarding an item having a problem in the health-level and the like is transmitted to the terminal of the beauty parlor (beauty salon) or the product development company. The hair health examination result and the like are also recorded in the personal record to be stored. The beauty parlor or the product development company can make good use of the thus obtained result for their services or development of a new product. Besides, the information can be fed back to each customer. In this feedback, a solution for improving the health condition of the customer (including products such as health foods and drinks, and supplements, and various services) can be provided together with the examination result and the analysis data.

EXAMPLES

<Hair Evaluation 1 Based on Morphological Characteristic of Hair Shaft>

Morphological characteristics of hair depending on respective hair types and hair types converted due to androgenetic alopecia (AGA) were examined. Specifically, hair was collected from the parietal region of a male subject in his thirties clinically diagnosed as non-AGA according to practice guidelines for AGA and having hair in a normal state. The collected hair included both black and white hairs, which were equivalent in the morphology of the medulla and the diameter of the hair shaft. Besides, a black hair was similarly collected from the parietal region of a male subject in his twenties clinically diagnosed to be a juvenile AGA patient. Furthermore, a normal black hair of the occipital region and a body hair of the inside of the forearm were also collected from the same AGA patient. The structures of these hairs were observed with an optical microscope. Results are illustrated in FIG. 1.

As illustrated in FIG. 1, a medulla having a prescribed thickness was present in a center portion of the white hair collected from the parietal region of the non-AGA male and the normal black hair collected from the occipital region of the AGA patient, but a medulla was lost or discontinuous in the hair of the parietal region of the AGA patient as in the body hair of the inside of the forearm. Thus, it was found that the hair had been changed to vellus hair like body hair. Accordingly, when the state of a medulla is observed, the health-level of the hair, namely, the presence or absence of tendency of alopecia caused by aging or juvenile alopecia, and the like can be determined. Besides, in one and the same patient, when hair of the occipital region used as a normal control is compared with hair of the parietal region, the health-level of the hair of the patient can be determined. In addition, it is understood that, in the hair of the occipital region of even the AGA patient, as described above, the medulla keeps a certain thickness and the hair is comparatively difficult to be affected by a hair diseases such as alopecia. Therefore, it can be said that hair of the occipital region is preferably used for measuring the health-level in regard of a disease excluding the hair diseases such as alopecia. Incidentally, "*" illustrated in FIG. 1 corresponds to a medulla of hair having a continuous structure. An arrow points to a discontinuous medulla, with an arrowhead indicating a structure presumed as a trace of the medulla.

<Hair Evaluation 2 Based on Morphological Characteristic of Hair Shaft>

Hairs were collected from the parietal region of subjects different in the age and the sex to examine morphological characteristics of the hairs. Specifically, hairs were collected from the occipital region of a plurality of females in their thirties and males in their fifties, and the structures of these hairs were observed with an optical microscope. In each hair, change of the hair shaft structure in accordance with a distance from the hair root was also checked. The results are illustrated in FIGS. 2 to 5.

Figure 2:
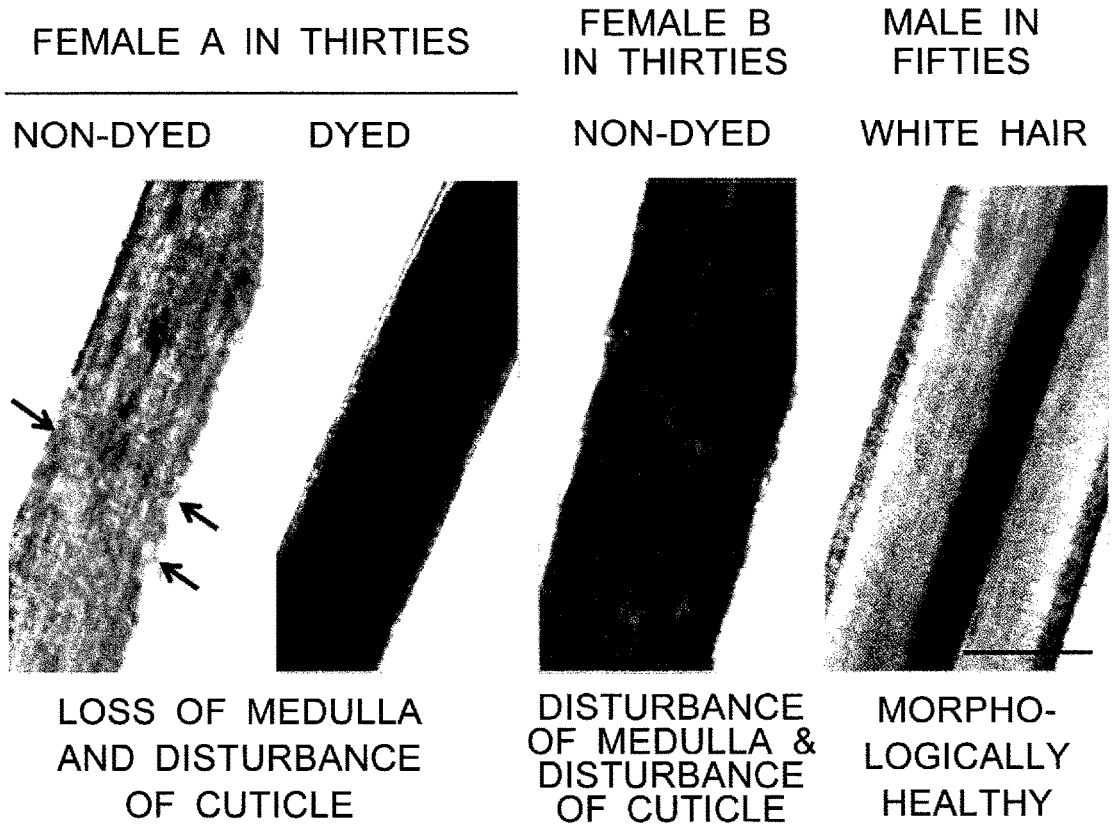
FIG. 2 is a diagram illustrating forms of medullas of hairs of subjects of different ages and sexes.
Figure 3:
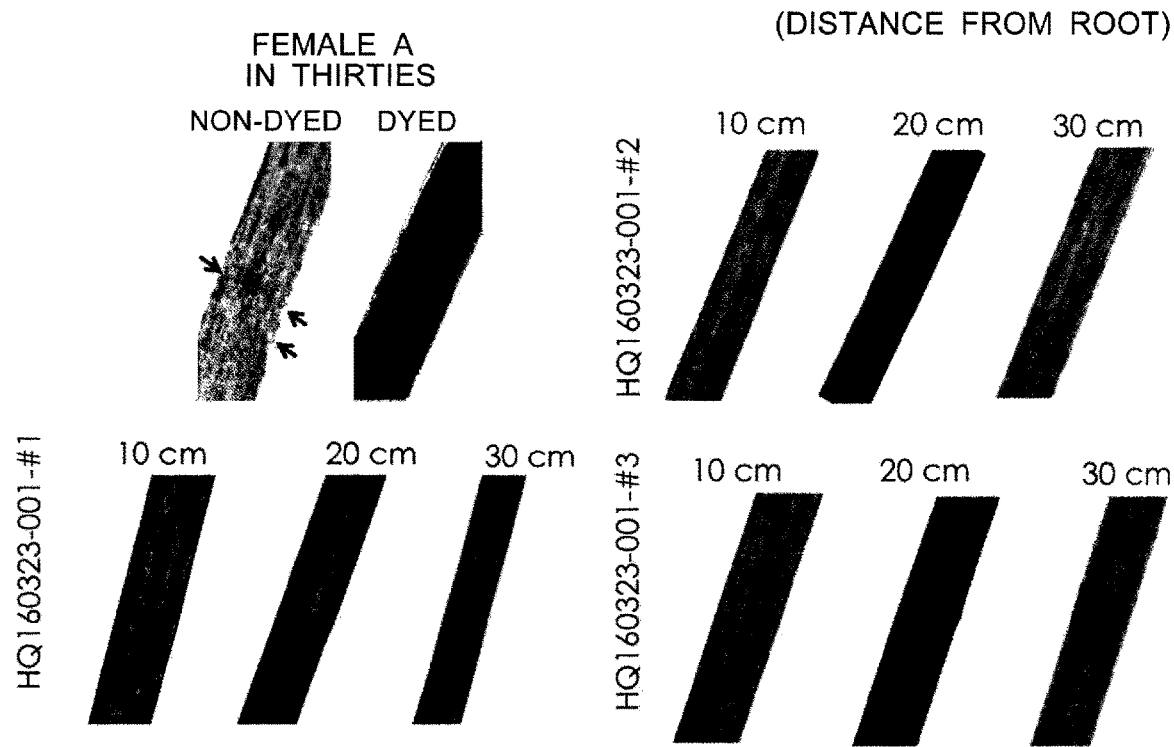
FIG. 3 is a diagram illustrating a form of a medulla of hair of a subject.
Figure 4:
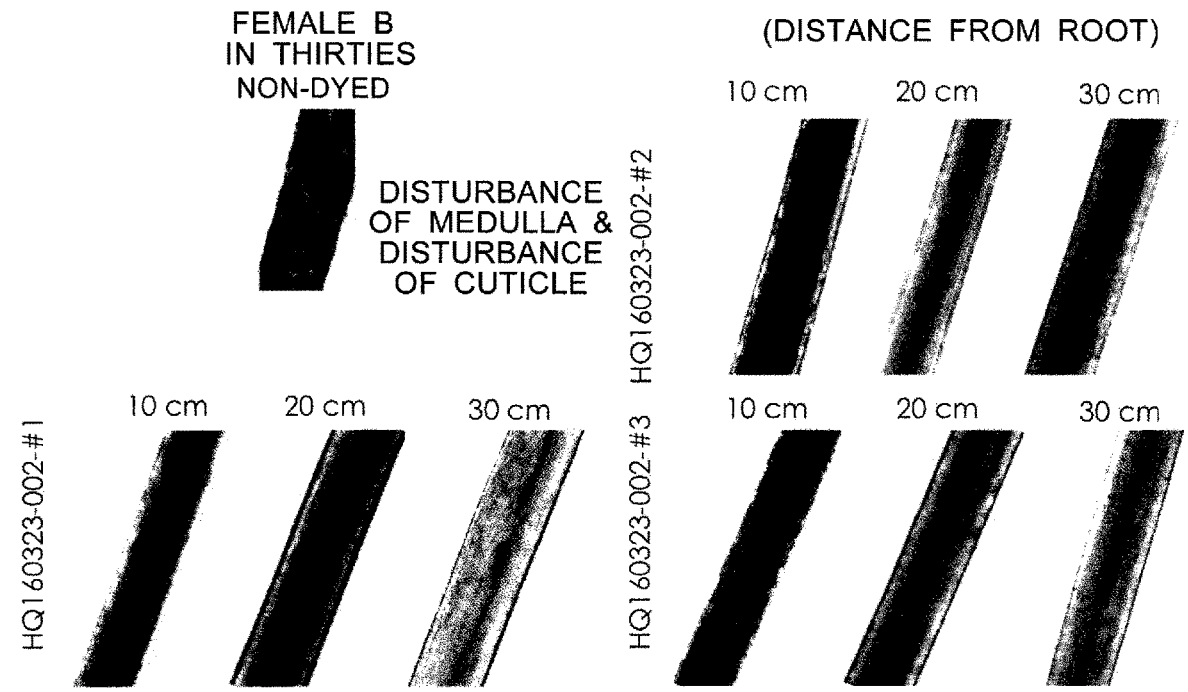
FIG. 4 is a diagram illustrating a form of a medulla of hair of a subject.
Figure 5:
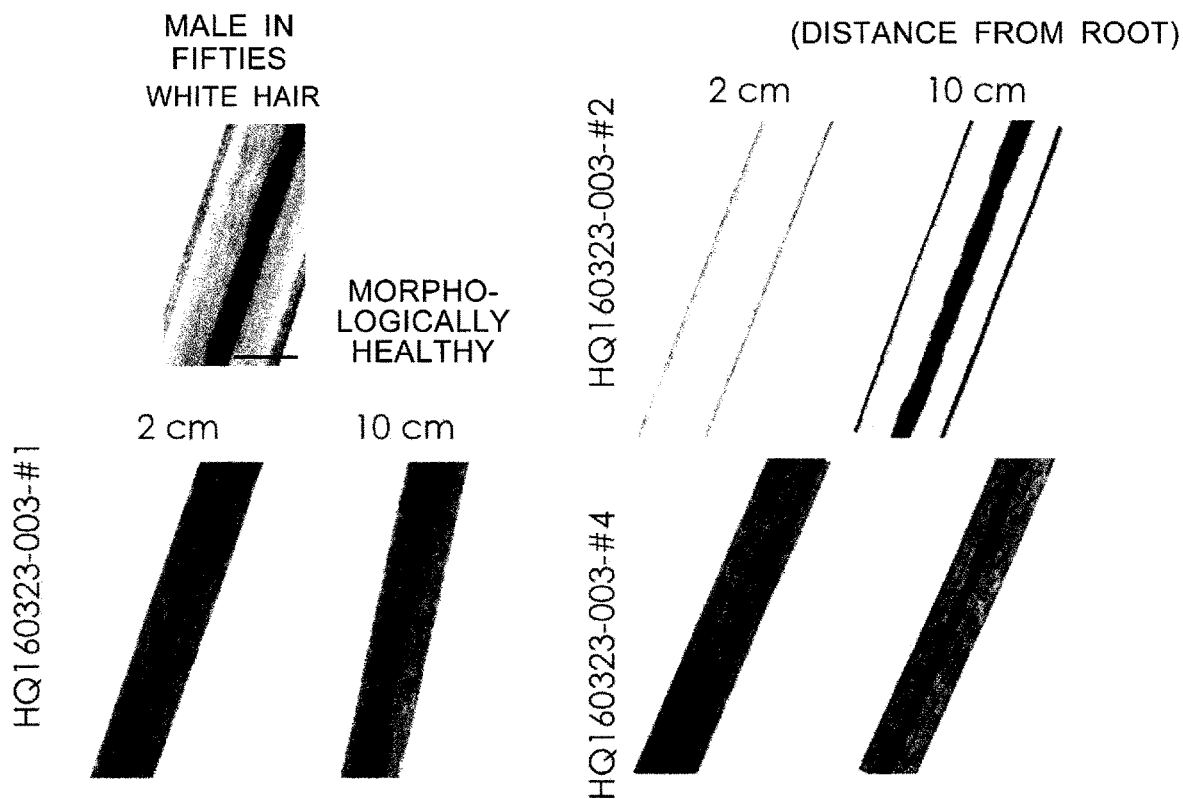
FIG. 5 is a diagram illustrating a form of a medulla of hair of a subject.

As illustrated in FIG. 2, when the hair collected from the occipital region or a region affected by non-androgenetic alopecia was observed with an optical microscope, the loss of a medulla or the disturbance of cuticles could be checked. For example, in a female A in her thirties, medullas clearly continuous were found in the vicinity of the root of the hair but medullas became deficient or discontinuous toward the tip of the hair. In a female B in her thirties, continuous medullas were found over the whole length from the root to the tip of the hair, but the cuticle structure was unclear or deficient. In a male in his fifties, clear medullas were found, and cuticles were found to be healthy. Besides, in the females A and B, the hairs kept substantially the same thickness from the vicinity of the root (at a distance of 10 cm from the root) to the tip (at a distance of 30 cm from the root) as clear from the hair shown in FIGS. 3 and 4, which reveals that hair type change had not been caused over the whole of a growth period of 20 months obtained through calculation. On the contrary, as illustrated in FIG. 5, in the male in his fifties, medullas found in the vicinity of the tip of the hair were deleted in the root, and in addition, the diameter of the hair shaft was reduced, which reveals that change into vellus hair analogous to androgenetic alopecia was progressing due to aging.

These results reveal that the hair type is changed or the thickness of hair is reduced due to aging because of the deletion of medullas and the diameter change of the hair shaft. In particular, in the male in his fifties illustrated in FIG. 5, it is suggested that the hair type change was caused at least within the past five months. In this manner, when a situation of hair from the root to the tip is observed and measured, a time period when the hair quality change was caused in the past can be specified.

<Quantitative Evaluation of Hair Quality Change Due to Aging—Melanin Granule Alignment>

In order to reveal that hair quality change due to aging can be quantitatively evaluated, attention was paid to the regularity of alignment of melanin granules of the medulla, and a relation between a ratio of a region where abnormality was caused and aging was analyzed using an ideal experimental sample. Specifically, an awl or guard hair shaft was collected from the back skin of C57BL/6 mice of various ages in week, and regularities of a hard keratin accumulation region that forms the medulla and is identifiable as a ladder-shaped structure and a colored region containing granules of melanin and the like were analyzed. The collected hair shafts were dispersed in 99.5% ethanol, and after washing to remove dirt from the surface, the resultant ethanol solution was transferred onto an APS coated slide glass (Matsunami Glass Ind., Ltd.). The hair shaft samples were dispersed so as to avoid overlapping with each other, and the resultant was air-dried under an air stream for about 5 minutes. The dried hair shaft samples were mounted using a water-soluble mounting medium, such as a 90% glycerol PBS solution, or distilled water and a cover glass. In awl or guard hair, the hard keratin accumulation region forming the medulla and the granule region form a regularly repeating structure, and the maximum number of lines of the granule region is constant depending on the hair type. Assuming that the number of lines and the arrangement of the repeating structure create a rhythm, the number of lines may locally become abnormal or the repeating structure may become unclear. A ratio occupied by such a rhythmic abnormal region in the observed length of the hair shaft was measured and plotted with respect to ages in week for comparison. As a microscope image of the awl or guard hair, a portion corresponding to the maximum diameter in each hair sample was selected. Besides, it was qualitatively found that abnormal alignment of the medullas of hair, which appears at extremely low frequency in a young mouse, occasionally appear in an old mouse. Therefore, in order to reveal whether or not quantitative determination could be made, a region where peculiar medulla of hair alignment abnormality caused the maximum displacement was selected to shoot a microphotograph. As for the presence of the regularity, three researchers having studied hair for 1 year or more individually identified an abnormal region in the same image data, and an average value of ratios occupied by the abnormal regions was measured. The results are illustrated in FIG. 6.

Figure 6:
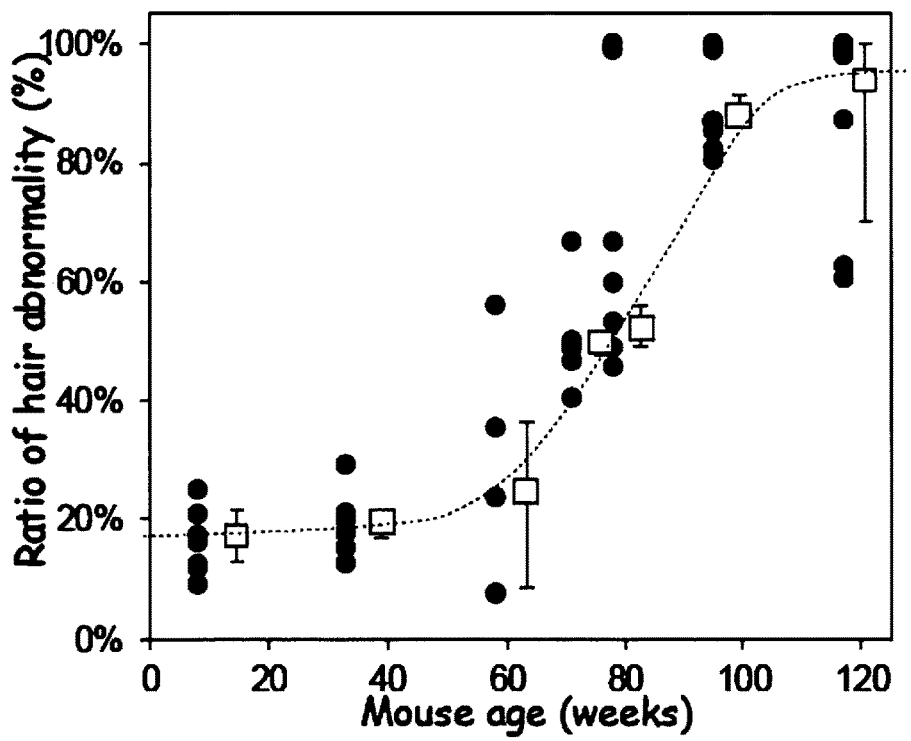
FIG. 6 is a diagram illustrating correlation between the age in week of a mouse and change of a regularity of a hair shaft.

As illustrated in FIG. 6, there was clear correlation between the aging of mice and the change of the regularity of the medulla of hair structure, which revealed that abnormality, caused by aging, of the rhythm in the hair shaft production can be quantitatively determined for comparison.

<Quantitative Evaluation of Hair Quality Change Due to Aging—Ratio of Abnormal Structure>

Figure 7:
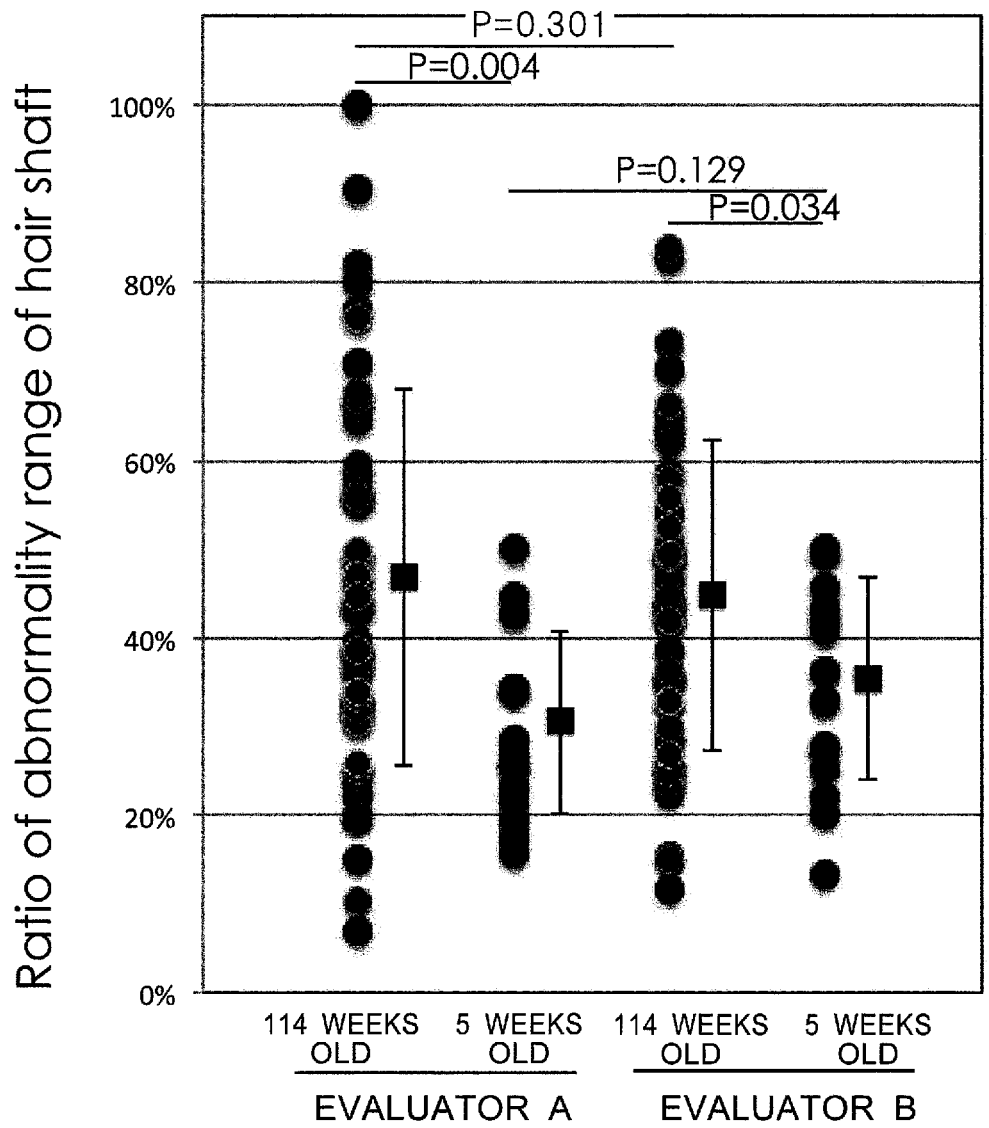
FIG. 7 is a diagram illustrating correlation between the age in week of a mouse and a ratio of structural abnormality of a hair shaft.

An abnormal region peculiar to old mice was detected so as to cause the maximum difference in an imaged region in FIG. 6, and thus, it was revealed that the change of the rhythmic regularity caused in the medulla of hair can be detected. In this experiment, with subjectivity eliminated, a center portion of a hair shaft having the maximum diameter was defined as an observation site, and microscope images of individual hair shafts were randomly obtained. Besides, the hair quality change of the medulla was defined as inconsistency of the medulla alignment (abnormality of the number of medulla disks, insertion of medulla disks, deletion of medulla disks), fusion or complexation of medulla disks (fusion in a direction horizontal or vertical to the hair axis), or obscureness of the disk structure (obscureness of a boundary between the (colorless) hard keratin accumulation region of the medulla and the colored granule region), and a ratio of a range occupied by a region having the abnormalities was evaluated. Besides, a researcher having hair research history of 10 or more years (evaluator A) and a researcher having hair research history less than 1 year (evaluator B) respectively measured a ratio of an abnormal structure of hair of a C57BL/6 mouse caused by aging through independent evaluation. Specifically, the change of the medulla rhythm was detected in 5-week-old and 105-week-old mice, and both the evaluators found that abnormality of the rhythm of the medulla structure not found in the young mouse was found in the old mouse, and regions detected as the abnormal region by these evaluators were common in 85%. The results are illustrated in FIG. 7.

It cannot be denied that the presence of the regularity of the medulla of hair was determined in FIG. 6 largely from subjective viewpoints of the researchers practicing the experiment. On the other hand, in this experiment, as illustrated in FIG. 7, criteria for the evaluation of the hair quality was clarified and hence a difference between the evaluators could be reduced. Besides, it was found that a ratio of the abnormal structure per unit length of the hair of a mouse is remarkably increased by aging.

<Quantitative Evaluation of Hair Quality Change Due to Aging—Change of Distance Between Inflection Points>

Hair of a mouse is classified, depending on the size of the hair shaft, the structure of the medulla and the number of inflection points, into three types of awl/auchen, guard and zigzag hairs. Among these hairs, the zigzag hair occupies about 70 to 80%. The zigzag hair has three inflection points, and is characterized by that the granule region of the medulla is aligned in one row. Such inflection points seem to be a hair quality characteristic similar to wavy hair of a human. Such an inflection point is formed also at a constant time interval, and hence has rhythmic regularity in the same manner as the medulla structure. Therefore, in order to quantitatively evaluate the hair quality change caused by aging, the change of a distance between inflection points in hair was measured to quantitatively evaluate the change in accordance with the age in week. Specifically, in the same manner as in the evaluation of the medulla structure, a hair shaft sample was mounted using an APS coated glass, a length from the tip to the first inflection point, a length from the first inflection point to the second inflection point, a length from the second inflection point to the third inflection point, and a length from the third inflection point to the root were measured and plotted, so as to compare an old mouse (114 weeks old) with a young mouse (5 weeks old) in positions where the inflection points appeared. The results are illustrated in FIG. 8.

Figure 8:
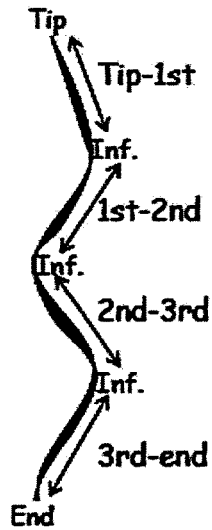
FIG. 8 is a diagram illustrating change of an distance between inflection points of the hair caused by aging.
Figure 8:
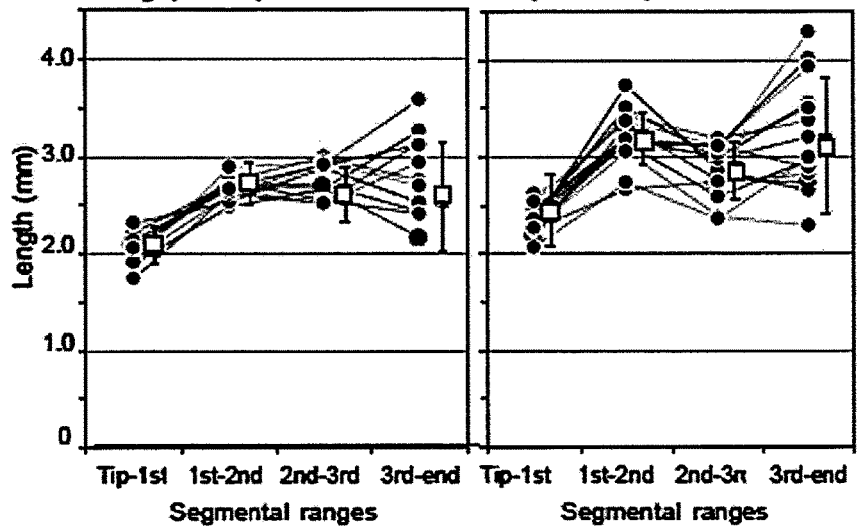
Figure 8:
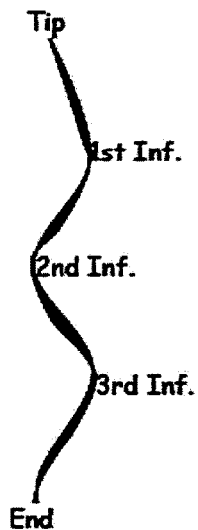
Figure 8:
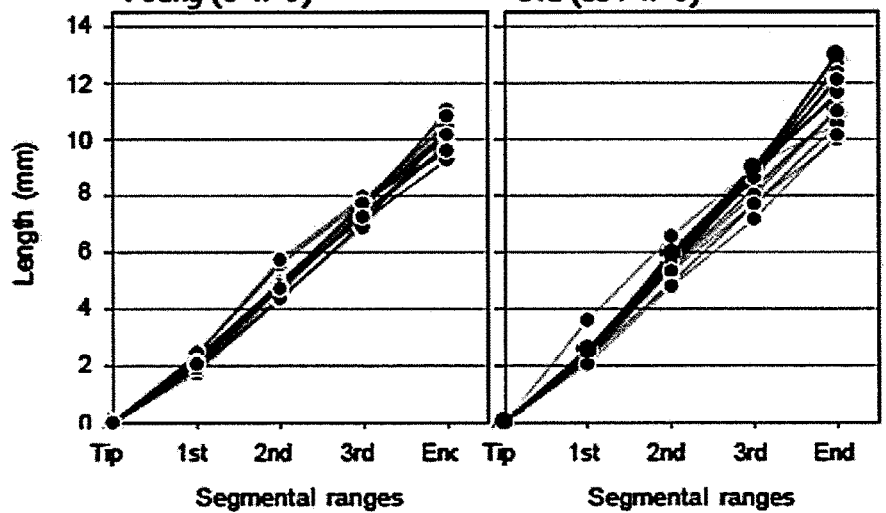

As illustrated in FIG. 8, it was found that the distance between inflection points tends to be longer in the old mouse. It is suggested that the distance between inflection points is elongated due to increase of the rhythmic irregularity in the medulla of hair.

INDUSTRIAL APPLICABILITY

According to a health-level measurement method of the present invention, a highly reliable health examination result based on scientific ground can be provided by using hair analysis, that is, a non-invasive and easier method. In particular, hair can be regarded as a storage medium in which all information ranging from the present to a given past time period is stored, and therefore, according to the present invention, information on change of the health condition of a subject can be provided. Besides, when information obtained from hair is linked to various big data, a solution suitable for each individual can be provided. Furthermore, a novel product based on scientific ground can be developed in the fields of health care, hair care and the like.

REFERENCE SIGNS LIST 1 health-level determination apparatus
2 hair analysis means
3 input means
4 comparison means
5 internal DB
6 external DB
7 determination means
8 communication means

The invention claimed is:

1. A method for determining the health-level of a subject, comprising:
   a hair analysis step (A) of analyzing hair of the subject, wherein the hair analysis is at least one selected from the group consisting of external structure analysis, internal structure analysis, strength of the hair, suppleness of the hair, a diameter of a hair shaft, a cross-sectional shape of the hair and a wavy state of the hair, genetic analysis and analysis of proteins, lipids, pigments and metabolites; and
   a determining step (B) of determinizing a health level selected from a risk of a specific disease, a risk of development of a specific disease, a state of stress, degree of aging and degree of fatigue from information obtained from said hair analysis step (A).

2. The method according to claim 1, wherein the hair analysis step (A) includes a substep (A-1) of analyzing hair of an occipital region.

3. The method according to claim 2, wherein the hair analysis step (A) further includes a substep (A-2) of analyzing hair of a region other than the occipital region.

4. The method according to claim 1, wherein the hair to be used for the hair analysis has undergone a marking treatment for specifying a time period.

5. The method according to claim 1, further comprising a comparison step (B) of comparing analysis data obtained in the hair analysis step (A) with analysis data of a population.

6. The method according to claim 1, wherein the external structure analysis is analysis of at least one selected from the group consisting of a cuticle and an optical characteristic.

7. The method according to claim 1, wherein the internal structure analysis is analysis of at least one selected from the group consisting of a cortex of hair, a medulla of hair, a melanin granule and a regularity of a hair shaft structure.

8. The method according to claim 7, wherein the regularity of the hair shaft structure is a structural regularity having a hierarchy derived from a hair production rhythm.

9. The method according to claim 1, wherein the composition analysis is analysis of at least one selected from the group consisting of minerals, proteins, lipids, pigments and metabolites.

10. The method according to claim 1, wherein the hair analysis includes at least internal structure analysis.

11. A health-level determination apparatus, comprising:
   a processor configured to:
      receive input of analysis data of hair of a subject; and
      determine the health-level of the subject selected from a risk of a specific disease, a risk of development of a specific disease, stress, aging and fatigue by comparing the analysis data of the subject that is input with a distribution of analysis data of a population,
      wherein the analysis data of the hair is at least one selected from the group consisting of external structure analysis data, internal structure analysis data, strength of the hair, suppleness of the hair, a diameter of a hair shaft, a cross-sectional shape of the hair and a wavy state of the hair, genetic analysis data and analysis data of proteins, lipids, pigments and metabolites.

12. A hair health examination system, comprising:
a processor configured to:
receive input of analysis data of hair of a subject;
perform comparison of the analysis data of the subject that is input with a distribution of analysis data of a population; and
determine the health-level of the subject selected from a risk of a specific disease, a risk of development of a specific disease, stress, aging and fatigue on the basis of a result of the comparison,
wherein the processor determines deviation of a state or a constitution of the subject by using, as the distribution of the analysis data of the population, a distribution of analysis data of other persons generated by taking the other persons as subjects, and determines change of the state or the constitution of the subject by using, as the distribution of the analysis data of the population, a distribution of the analysis data of the subject himself/herself collected in an evaluation period during which the state or the constitution of the subject is evaluated,
wherein the analysis data of the hair is at least one selected from the group consisting of external structure analysis data, internal structure analysis data, strength of the hair, suppleness of the hair, a diameter of a hair shaft, a cross-sectional shape of the hair and a wavy state of the hair, genetic analysis data and analysis data of proteins, lipids, pigments and metabolites.

* * * * *